United States Patent [19]
Chang et al.

[11] Patent Number: 5,994,394
[45] Date of Patent: Nov. 30, 1999

[54] POLYHETEROCYCLIC COMPOUNDS

[75] Inventors: Ching Te Chang, Taipei; Yuh-Lin Yang, Hsin Chu Hsien, both of Taiwan

[73] Assignee: Industrial Technology Research Institute, Taiwan

[21] Appl. No.: 08/821,472

[22] Filed: Mar. 21, 1997

[51] Int. Cl.$^6$ .......................... A61K 31/34; A61K 31/38; C07D 307/36; C07D 307/40
[52] U.S. Cl. .......................... 514/444; 514/461; 549/60; 549/472; 549/473
[58] Field of Search .......................... 549/60, 472, 473; 514/444, 461

[56] References Cited

U.S. PATENT DOCUMENTS

| | | | |
|---|---|---|---|
| 3,050,442 | 8/1962 | Biiloo et al. | 167/33 |
| 4,937,256 | 6/1990 | Kober et al. | 514/444 |
| 5,508,440 | 4/1996 | Chang et al. | 549/59 |
| 5,578,636 | 11/1996 | Chang et al. | 514/444 |
| 5,596,014 | 1/1997 | Chang et al. | 514/444 |
| 5,602,170 | 2/1997 | Chang et al. | 514/444 |

FOREIGN PATENT DOCUMENTS

| | | |
|---|---|---|
| 0 344 660 A1 | 12/1989 | European Pat. Off. . |
| 4-46165 | 2/1992 | Japan . |
| 5-204175 | 8/1993 | Japan . |
| WO 95/32001 | 11/1995 | WIPO . |

OTHER PUBLICATIONS

Kooreman et al, "Recl. Trav. Chim. Pays–Bas", 86 (1) pp. 37–55, 1967.
Krasnaya, et al. Chemical Abstracts, 68:78046t (1968).
Venters et al., Chemical Abstracts, 73:31375n (1970).
Atkinson et al., Chemical Abstracts, 74:111197s (1971).
Tertov et al., Chemical Abstracts, 75:49163t (1971).
Shkrebets et al., Chemical Abstracts, 80:133364v (1974).
L. V. Kozhevnikov, Chemical Abstracts, 85:159799u (1985).
Kretchmer et al., Chemical Abstracts, 85:62770q (1976).
I. V. Kozhevnikov, Chemical Abstracts, 86:120465c (1977).
Seppo I. Pennanen, Chemical Abstracts, 88:136386e (1978).
Osipov et al., Chemical Abstracts, 89:24070m (1978).
Kauffmann et al., Chemical Abstracts, 89:43185u (1978).
Kauffmann et al., Chemical Abtracts, 96:34993y (1982).
El–Hajj et al., Chemical Abstracts, 98:197914d (1983).
Itahara, et al., Chemical Abstracts, 101:110661c (1984).
Huffman et al., Chemical Abstracts, 102:185592k (1985).
Jaouhari et al., Chemical Abstracts, 106:67026p (1987).
Vogel et al., Chemical Abstracts, 108:204388r (1988).
Tymyanskii et al., Chemical Abstracts, 109:170154q (1988).
Melikyan et al., Chemical Abstracts, 112:178501h (1990).
Merrill et al., Chemical Abstracts, 112:198028n (1990).
Chang et al., Chemical Abstracts, 112:35586d (1990).
Shabana, et al., Chemical Abstracts, 113:191079s (1990).
John O. Morely, Chemical Abstracts, 115:233419b (1991).
Johnson et al., Chemical Abstracts, 117:69843d (1992).
Ogura et al., Chemical Abstracts, 117:26322r (1992).
Ogura et al., Chemical Abstracts, 117:69716q (1992).
Joshi et al., Chemical Abstracts, 119:117997x (1993).
Miller et al., Chemical Abstracts, 120:298617n (1994).
Miller et al., Chemical Abstracts, 120:217639w (1994).
Amano et al., Chemical Abstracts, 120:41968m (1994).
Sanderson et al., Chemical Abstracts, 122:215519z (1995).
Fort et al., Chemical Abstracts, 122:81080p (1995).
El–Hajj et al., "Dérivés de L'hydroxyméthyl–5 furfural", J. Heterocyclic Chem., 20:223 (1983).
Jaouhari et al., "Carbon–Carbon Coupling and Alkylation of Furan and Thiophene, invloving C–H Bond Activation, with Ruthenium Catalysts in Alcohols", J. Chem.Soc., Chem.Commun. pp. 1255–1257 (1986).
Miller et al., "The Observation of a Thermal 'Double Aromatization' Process in a Hydrocarbon with Fused Blocked Aromatic Rings", J. Chem.Soc., Chem.Commun. p. 1257 (1986).
Joshi et al., "Synthesis, Electrical Conductivity and Electron Paramagnetic Resonance Spectroscopy of Polymers derived from $NOPF_6$–Doped XYZ–Triheterocycles Based on Pyrrole, Furan and Thiophene", J.Chem.Soc.Perkin Trans. pp. 1081–1086 (1993).
McFarland et al., "Reactions of 2,2',5',2"—Terfuran", J. Heterocyclic Chem. 32:1747–1750 (1995).
Carter et al., #2684, Proceedings of the American Association for Cancer Research, vol. 37, Mar. 1996.
Waters et al., #2705, Proceedings of the American Association for Cancer Research, vol. 37, Mar. 1996.
Hudson et al., "Biological activities of terthiophenes and polyynes from the Asteraceae", Chemical Abstracts vol. 120, abstract No. 4283, XP002069097.

*Primary Examiner*—Ba K. Trinh
*Attorney, Agent, or Firm*—Fish & Richardson P.C.

[57] ABSTRACT

The present invention relates to a group of polyheterocyclic compounds covered by the following formula:

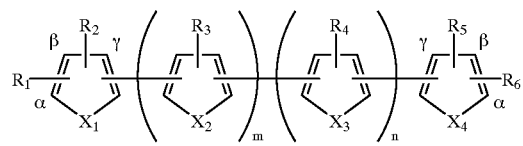

wherein each of $X_1$, $X_2$, $X_3$, and $X_4$, independently, is O, S, NH, or $N(C_{1-6}$alkyl), but one of them must be O, NH, or $N(C_{1-6}$ alkyl); each of $R_1$, $R_2$, $R_5$, and $R_6$, independently, is H or a substituent (e.g., halogen, CN, $NO_2$, or $C_{1-4}$ haloalkyl), but at least one of them must be a substituent; each of $R_3$ and $R_4$, independently, is H, $C_{1-6}$ alkyl, CHO, $CH_2OH$, or $CH_2NH_2$; and each of m and n, independently, is 0 or 1.

33 Claims, No Drawings

POLYHETEROCYCLIC COMPOUNDS

BACKGROUND OF THE INVENTION

The treatment of cancer can be approached by several modes of therapy including surgery, radiation, chemotherapy or a combination of any of these treatments. Chemotherapy continues to be an indispensable therapy for inoperable or metastatic forms of the disease.

Considering the diversity of tumors in terms of cell type, morphology, growth rate and other cellular characteristics, the U.S. National Cancer Institute ("NCI") has developed a "disease-oriented" approach to antitumor activity screening [M. R. Boyd, in "Principle of Practice of Oncology," J. T. Devita, S. Hellman, S. A. Rosenberg (Eds.) Vol. 3, PPO Update, No. 10, 1989]. This in vitro screening system is based on the measurement of antitumor cytotoxicity against human tumor cell line panels consisting of approximately 60 cell lines of major human tumors (including leukemia and slower growing tumor cells such as lung, colon, breast, skin, kidney, etc.). The most important advantage of the new in vitro screening panels is the opportunity to identify compounds that are selectively more cytotoxic to cells of slowly growing solid tumors than to rapidly growing leukemia cells.

Thiophenes are sulfur containing heterocyclic compounds that are distributed widely among the species of the Asteraceae (Compositaie) family, including many species with known medicinal uses. The natural thiophene compounds are thought to play an important role in the chemical defense of plants against herbivorous insects and other pests. Natural thiophenes have been previously described as having cytotoxic activities upon exposure to long wavelength ultraviolet light. Photochemical studies suggest that thiophene phototoxicity is based primarily on the production of toxic singlet oxygen by a type II photodynamic process.

However, polythiophene compounds also exhibit cytotoxic activity in the absence of light activation.

We have prepared polyheterocyclic compounds (i.e., containing at least two heterocyclic rings) based on natural polythiophenes and tested their efficacy in inhibiting the growth of tumor cells employing the above-described NCI screening system.

SUMMARY OF THE INVENTION

An aspect of the present invention relates to a group of polyheterocyclic compounds covered by the following formula:

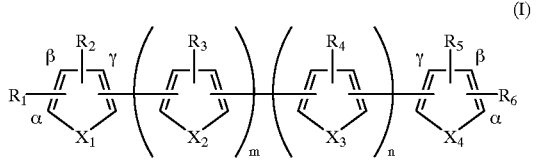

(I)

wherein each of $X_1$, $X_2$, $X_3$, and $X_4$, independently, is O, S, NH, or N($C_{1-6}$ alkyl);

each of $R_1$, $R_2$, $R_5$, and $R_6$, independently, is H, halogen, CN, $NO_2$, $C_{1-4}$ haloalkyl, $CR^aR^b(CH_2)_oNR^cR^d$, $NR^cR^d$, $CR^a$=$NR^c$, $CR^a$=$N^+R^cR^d$, $CR^aR^b(CH_2)_oOR^e$, $CR^aR^b(CH_2)_oO(C_{1-7}$ acyl), $CR^aR^b(CH_2)_oO$ (tetrahydropyranyl) (the C atom at position 2 of the tetrahydropyranyl moiety is bonded to its neighboring O atom), $OR^e$, $O(C_{1-7}$ acyl), $C(O)R^e$, $C(O)OR^e$, $CH(OR^e)_2$, CH=$CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine (e.g., pyrrolidine, piperidine, or piperazine; the cyclic amine can be bonded to the neighboring N atom via any of its atoms), or $R^c$ and $R^d$, together, are —$(CH_2)_4$—, —$(CH_2)_5$—, or —$(CH_2)_2NH(CH_2)_2$— (in other words, $R^c$ and $R^d$, together with their neighboring N atom, form a $C_{4-5}$ cyclic amine, i.e., pyrrolidine, piperidine, or piperazine); each $R^e$, independently, is H or $C_{1-6}$ alkyl; $R^f$ is $C(O)R^e$, CN, $NO_2$, $C_{4-5}$ cyclic amine (e.g., pyrrolidine, piperidine, or piperazine; preferably, the cyclic amine is bonded to the neighboring C atom via its N atom), or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;

each of m and n, independently, is 0 or 1;

provided that at least one of $X_1$, $X_2$, $X_3$, and $X_4$ is O, NH, or N($C_{1-6}$ alkyl), $X_1$, $X_2$, $X_3$, and $X_4$ are not all identical, and at least one of $R_1$, $R_2$, $R_5$, and $R_6$ is a substituent.

A subset of the above-described compounds are featured by that each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is C4-5 cyclic amine; each of $R_3$ and $R_4$, independently, is $CH_2OH$ or $CH_2NH_2$; m is 1; and n is 0. Preferably, each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$CH_2)_2NH(CH_2)_2$—; and each $R^e$, independently, is H.

Another subset of the above-described compounds are featured by that $R_1$ is H, $R_2$ is H, and each of $R_5$ and $R_6$, independently, is a substituent. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$. independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; m is 1; and n is 0. More preferably, each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

A further subset of the above-described compounds are featured by that $R_1$ is H, $R_5$ is H, and each of $R_2$ and $R_6$, independently, is a substituent; provided that if $R_2$ is a α-substituent, $R_6$ must be a β- or γ-substituent; if $R_2$ is a β-substituent, $R_6$ must be a α- or γ-substituent; and if $R_2$ is a γ-substituent, $R_6$ must be a α- or β-substituent. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO$ ($C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; m is 1; and n is 0. More preferably, each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

Yet another subset of the above-described compounds are featured by that at least two of the heterocyclic moieties are joined to each other via an α-β linkage. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)OR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; m is 1; and n is 0. More preferably, each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

Another aspect of the present invention relates to polyheterocyclic compounds also covered by formula (I), supra, wherein each of $X_1$, $X_2$, $X_3$, and $X_4$, independently, is O, S, NH, or $N(C_{1-6}$ alkyl);

each of $R_1$, $R_2$, $R_5$, and $R_6$, independently, is H, halogen, CN, $NO_2$, $C_{1-4}$ haloalkyl, $CR^aR^b(CH_2)_oNR^cR^d$, $NR^cR^d$, $CR^a$=$NR^c$, $CR^a$=$N^+R^cR^d$, $CR^aR^b(CH_2)_oOR^e$, $CR^aR^b(CH_2)_oO(C_{1-7}$ acyl), $CR^aR^b(CH_2)_oO$(tetrahydropyranyl), $OR^e$, $(C_{1-7}$ acyl), $C(O)$ $R^e$, $C(O)OR^e$, $CH(OR^e)_2$, CH=$CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are —$(CH_2)_4$—, —$(CH_2)_5$—, or —(CH2)2NH(CH2)2—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;

m is 1; and n is 0 or 1;

provided that at least one of $X_1$, $X_2$, $X_3$, and $X_4$ is O, NH, or $N(C_{1-6}$ alkyl), and at least one of $R_1$, $R_2$, $R_5$, and $R_6$ is a β-substituent.

A subset of the above-described compounds are featured by that each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)OR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or —$(CH_2)_4$—, —$(CH_2)_5$—, or —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; and n is 0. Preferably, each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

Another subset of the above-described compounds are featured by that at least two of the heterocyclic moieties are joined to each other via an α-β linkage. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; and n is 0. More preferably, each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

A still another aspect of this invention relates to a pharmaceutical composition which contains a pharmaceutically acceptable carrier and an effective amount of at least one of the polyheterocyclic compounds of formula (I), supra, wherein each of $X_1$, $X_2$, $X_3$, and $X_4$, independently, is O, S, NH, or $N(C_{1-6}$ alkyl);

each of $R_1$, $R_2$, $R_5$, and $R_6$, independently, is H, $C_{1-6}$ alkyl, halogen, CN, $NO_2$, $C_{1-4}$ haloalkyl, $CR^aR^b(CH_2)_oNR^cR^d$, $NR^cR^d$, $CR^a$=$NR^c$, $CR^a$=$N^+R^cR^d$, $CR^aR^b(CH_2)_oOR^e$, $CR^aR^b(CH_2)_oO(C_{1-7}$ acyl) $CR^aR^b(CH_2)_oO$(tetrahydropyranyl), $OR^e$, $O(C_{1-7}$ acyl), $C(O)R^e$, $C(O)OR^e$, $CH(OR^e)_2$, CH=$CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are —$(CH_2)_4$—, —$(CH_2)_5$—, or —$(CH_2)_2NH(CH_2)_2$—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;

each of m and n, independently, is 0 or 1;

provided that at least one of $X_1$, $X_2$, $X_3$, and $X_4$ is O, NH, or $N(C_{1-6}$ alkyl), and at least one of $R_1$, $R_2$, $R_3$, and $R_6$ is a substituent.

A subset of the compounds which can be used in the above-described pharmaceutical composition are featured by that each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)OR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; and n is 0. Preferably, each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

Another subset of the compounds which can be used in the above-described pharmaceutical composition are featured by that $R_1$ is H, $R_2$ is H, and each of $R_5$ and $R_6$, independently, is a substituent. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; and n is 0. More preferably, each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

A still another subset of the compounds which can be used in the above-described pharmaceutical composition are featured by that $R_1$ is H, $R_5$ is H, and each of $R_2$ and $R_6$, independently, is a substituent; provided that if $R_2$ is a α-substituent, $R_6$ must be a β- or γ-substituent; if $R_2$ is a β-substituent, $R_6$ must be a α- or γ-substituent; and if $R_2$ is a γ-substituent, $R_6$ must be a α- or β-substituent. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; and n is 0. More preferably, each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

Yet another subset of the compounds which can be used in the above-described pharmaceutical composition are featured by that at least two of the heterocyclic moieties are joined to each other via an α-β linkage. Preferably, each of $X_1$, $X_2$, $X_3$, and $X_4$, independently, is O or S; each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine; each of $R_3$ and $R_4$, independently, is $CH_2OH$ or $CH_2NH_2$; and n is 0. More preferably, each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

Other than various polyheterocyclic compounds set forth above which can be used to treat tumors (e.g., leukemia, lung cancer, colon cancer, CNS cancer, melanoma, ovarian cancer, renal cancer, prostate cancer, and breast cancer), a method of treating tumor by administering to a patient the just-described pharmaceutical composition is also contemplated as an aspect of this invention. Within this invention too is the use of polyheterocyclic compounds for the manufacture of a medicament for the treatment of tumor.

Other features or advantages of the present invention will be apparent from the following detailed description of several embodiments, and also from the appending claims.

DETAILED DESCRIPTION OF THE INVENTION

The polyheterocyclic compounds described above can be prepared by methods well known in the art. For example, a terheterocyclic compound can be prepared by first coupling a properly functionalized furan, pyrrole, or thiophene, i.e., substituted with dihydroxyboryl/tributylstannyl and/or with one or two desired groups to a dibromo- or diiodofuran, pyrrole, or thiophene (the furan, pyrrole, or thiophene may be additionally substituted, if desired) with the two halogen groups located at desired positions to form a biheterocyclic compound—the two monoheterocyclic compounds being joined together via a bond which links the two carbon atoms at which the dihydroxyboryl/tributylstannyl group and one of the two halogens are positioned. The biheterocyclic compound is then coupled with another properly functionalized furan, pyrrole, or thiophene to form a terheterocyclic compound. Both the Suzuki coupling method [N. Miyaura and A. Suzuki, Chem. Rev. 95, 2457–2483, 1995] or the Stille coupling method [L. L. Miller and Y. Yu, J. Org. Chem. 60, 6813–6819, 1995; Z. Baso, W. K. Chan, and L. Yu, J. Am. Chem. Soc. 117, 12426–12435 1995; and J. K. Stille, Angew. Chem. Int. Ed. Engl. 25, 508–524, 1986] can be used to link two heterocyclic compounds as described above. The catalyst $PdCl_2(PPh_3)_2$ is used for the Stille coupling method, and $Pd(PPh_3)_4$ or $Pd(OAc)_2$ for the Suzuki coupling method.

Desired biheterocyclic or tetraheterocyclic compounds can be synthesized via the same coupling reactions using appropriately functionalized furan, pyrrole, or thiophene compounds, which are commercially available or can be readily prepared. Indeed, referring back to Formula (I), CH=$NR^cR^d$, $CH_2NR^cR^d$ and CH=CHCOO(alkyl) (three optional substituents for $R^1$) can be prepared from CHO, i.e., by reacting CHO with $HNR^cR^d$, by reacting CHO with $HNR^cR^d$ followed by sodium borohydride reduction, and by reacting CHO with an acetate derivative, respectively; and $CH_2O(C_{1-7}$ acyl) and $CH_2O$(tetrahydropyranyl) (two optional substituents for $R^1$) can be prepared by reacting $CH_2OH$ with an acylation agent in the former and by reacting $CH_2OH$ with dihydropyran in the latter. In any event, polyheterocyclic compounds disclosed herein can be prepared by methods analogous to those described in the literature or patents, such as U.S. Pat. No. 5,508,440, U.S. Pat. No. 5,578,636, U.S. Pat. No. 5,596,014, and U.S. Pat. No. 5,602,170.

As mentioned above, the present invention provides a pharmaceutical formulation having an effective amount of a polyheterocyclic compound for treating a patient having a tumor. As used herein, an effective amount of the polyheterocyclic compound is defined as the amount of the compound which, upon administration to a patient, inhibits growth of tumor cells, kills malignant cells, reduces the volume or size of the tumors, or eliminates the tumor entirely in the treated patient. The effective amount to be administered to a patient is typically based on body surface area, patient weight, and patient condition. The interrelationship of dosages for animals and humans (based on milligrams per meter squared of body surface) is described by Freireich, E. J., et al., Cancer Chemother. Rep., 50(4):219, 1966. Body surface area may be approximately determined from patient height and weight. See, e.g., Scientific Tables, Geigy Pharmaceuticals, Ardley, N.Y., pages 537–538, 1970. An effective amount of the ployheterocyclic compound in the present invention can range from about 5 mg/kg to about 500 mg/kg, more preferably from about 5 mg/kg to about 250 mg/kg, and most preferably about 5 to about 150 mg/kg. Effective doses will also vary, as recognized by those skilled in the art, dependant on route of administration, excipient usage, and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier.

Solubilizing agents such as cyclodextrins, which form specific, more soluble complexes with the present polyheterocyclic compounds, or other solubilizing agents well-know to those familiar with the art, can be utilized as pharmaceutical excipients for delivery of the therapeutic compounds.

The polyheterocyclic compound can also be formulated into dosage forms for other routes of administration utilizing well-known methods. The pharmaceutical composition can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with the conventional procedure by compressing mixtures of the active polyheterocyclic compound and a solid carrier, and a lubricant. Examples of solid carriers include starch and sugar bentonite. The polyheterocyclic compound can also be administered in a form of a hard shell tablet or capsule containing, for example, lactose or mannitol as a binder and a conventional filler and a tableting agent.

The carrier in the pharmaceutical composition must be "acceptable" in the sense of being compatible with the active ingredient of the formulation (and preferably, capable of stabilizing it) and not deleterious to the subject to be treated.

The antitumor activity of heterocyclic compounds described above can be preliminarily evaluated using an in vitro assay, and then confirmed by in vivo testing. For example, see U.S. Pat. No. 5,578,636.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein, including patents, are hereby incorporated by reference in their entirety.

EXAMPLE 1

Synthesis of 5-[2-(5-formyl)thienyl]-2,2'-bifuran (1) Synthesis of 2-(diethoxymethyl)-5-(tributylstannyl) thiophene A solution of 22.4 g (200 mmol) of 2-thiophene carboxaldehyde and 44.4 g (300 mmol) of triethyl orthoformate in ethanol (200 mL) with 3–5 drops of concentrated HCl was heated at reflux for 4 hrs. The reaction mixture was then neutralized with $K_2CO_3$. After filtered and concentrated, 33.5 g (90% yield) of 2-(diethoxymethyl)-thiophene was distilled under reduced pressure (bp 156° C./1 torr).

18.6 g (100 mmol) of 2-(diethoxymethyl) thiophene in 100 ml of tetrahydrofuran ("THF") was placed in a 2-neck flask equipped with dropping funnel. The solution was cooled to –78° C. under nitrogen atmosphere and added 62.5 mL of 1.6 M n-butyl lithium (100 mmol) dropwise through dropping funnel in 1 hr. The reaction mixture was stirred at –78° C. for 1 hr and gradually warmed up to room temperature. After stirred for 30 minutes, the mixture was again cooled to –78° C. and added dropwise a THF (50 mL) solution of 32.5 g (100 mmol) of tributyl tin chloride with continual stirring. Gradually warmed up to room temperature, the mixture was stirred for another 10–12 hrs at room temperature and then concentrated. Reduced pressure distillation yielded 36.8 g (80%) of 2-(diethoxymethyl)-5-(tributylstannyl) thiophene (bp 195° C./1 torr).

(2) Synthesis of dihydroxy-(2-furyl)borane

Furan (13.6 g, 200 mmol) in 100 mL of ether was placed in a 2-neck flask equipped with dropping funnel. The solution was cooled to –78° C. under nitrogen atmosphere and added 125 ml of 1.6 M n-butyl lithium (200 mmol) dropwise through dropping funnel in 1 hr. The reaction mixture was stirred at –78° C. for 1 hr and then gradually warmed up to room temperature. After stirred at room temperature for 30 minutes, the mixture was again cooled to –78° C. and added dropwise an ether (50 mL) solution of 37.0 g (200 mmol) of triisopropyl borate with continual stirring. Gradually warmed up to room temperature, the mixture was stirred at room temperature for another 4–6 hrs. After cooled to 0° C. and added 10% HCl solution, the mixture was stirred for 1 hr and then extracted with ether. The combined ether extracts were dried with anhydrous $MgSO_4$ and concentrated at room temperature to yield a viscous oil. Addition of n-hexane precipitated dihydroxy-(2-furyl) borane which was used for the next reaction without further purification.

$^1$H NMR (CDCl$_3$, 200 MHz): δ 4.73 (bs, 2H), 6.45 (dd, J=1.5, 3.3 Hz, 1H), 7.02 (d, J=3.3 Hz, 1H), 7.61 (d, J=1.5 Hz, 1H).

(3) Synthesis of 2,5-dibromofuran 120 mL of dimethylformamide ("DMF") was placed in a 2-neck flask equipped with dropping funnel and refluxing condenser and cooled to –20° C. Bromine (0.25 mol) was added with stirring. Stirring was continued for 2 hrs after the addition completed. In another 2-neck flask, equipped with dropping funnel and refluxing condenser, was placed 0.125 mol of furan and 100 mL of DMF. The furan solution was heated at 30–40° C. and dropped in the above prepared bromine solution through the dropping funnel slowly with stirring. After addition was completed, the mixture was stirred at 60° C. for 2 hrs and then extracted with ether. The combined ether extracts were washed with brine, dried with anhydrous $MgSO_4$ and concentrated to yield an oil which was chromatographed to yield 40% of 2,5-dibromofuran.

$^1$H NMR (CDCl$_3$, 200 MHz): δ 6.28 (S, 2H)

(4) Synthesis of 5-bromo-2,2'-bifuran

In a 2-neck flask was placed 2,5-dibromofuran (18.1 g, 80 mmol) with catalyst Pd(PPh$_3$)$_4$ (5 mol %) and added 30 mL of benzene and 6 mL of 2 M Na$_2$CO$_3$ aqueous solution. The mixture was added 2.2 g (20 mmol) of dihydroxy-2-(furyl) borane dissolved in 6 mL of methanol and heated at reflux for 12 hrs. Thin layer chromatography ("TLC") showed 2 fluorescent spots. The less polar spot was identified as the desired dimer product. The mixture was extracted with ether. The combined ether extracts were dried with anhydrous $MgSO_4$ and concentrated. The crude product was then used for the next reaction.

(5) Synthesis of 5-[2-(5-formyl)thienyl]-2,2'-bifuran

5-Bromo-2,2'-bifuran (0.21 g, 1 mmol), 2-(diethoxymethyl)-5-(tributylstannyl) thiophene (0.95 g, 2 mmol) and catalyst Pd(PPh$_3$)$_2$Cl$_2$ (5 mol %) were placed in a 2-neck flask with 50 mL of THF. The reaction mixture was heated at reflux for 12 hrs. TLC showed 2 fluorescent spots. The more polar spot was identified as the desired trimer product. The reaction was quenched with ammonium hydroxide solution and extracted with ether. The combined ether extracts were dried with anhydrous $MgSO_4$ and concentrated. Chromatograph yielded 50% of the desired product.

$^1$H NMR (CDCl$_3$, 200 MHz): δ 6.48 (dd, J=2.0, 3.6 Hz, 1H), 6.63 (d, J=3.6 Hz, 1H), 6.67 (d,J=3.5 Hz, 1H), 6.78 (d,J=3.5 Hz, 1H), 7.33 (d,J=4.0 Hz, 1H), 7.44 (d,J=2.0 Hz, 1H), 7.66 (d,J=4.0 Hz, 1H), 9.85 (s, 1H).

EXAMPLE 2

Synthesis of 5-[2-(5-hydroxymethyl)thienyl]-2,2'-bifuran

An ethanol solution (50 mL) of 5-[2-(5-formyl) thienyl]-2,2'-bifuran (0.088 g), obtained following the procedures described in Example 1, was added excess NaBH$_4$ under N$_2$ atmosphere and stirred at room temperature for 4 hrs. The reaction was quenched with ammonium chloride solution and extracted with ether. The combined ether extracts were dried with anhydrous MgSO$_4$ and concentrated to yield 90% of the desired solid product.

$^1$H NMR (CDCl$_3$, 200 MHz): δ 1.90 (bs, 1H), 4.80 (s, 2H), 6.45 (dd, J=1.9, 3.5 Hz, 1H), 6.51 (d, J=3.5 Hz, 1H), 6.57 (d,J=3.5 Hz, 1H), 6.59 (d,J=3.5 Hz, 1H), 6.92 (d,J=3.7 Hz, 1H), 7.14 (d,J=3.7 Hz, 1H), 7.41 (d,J=1.9 Hz, 1H).

EXAMPLE 3

Synthesis of 5-formyl-5'-(2-furyl)-2,2'-bithiophene (1) Synthesis of 2-(tributylstannyl) furan A THF solution (100 mL) of furan (6.8 g) was cooled to −78° C. under N$_2$ atmosphere. Butyl lithium (1.6 M×62.5 mL, 100 mmol) was added dropwise through dropping funnel in 1 hr. After stirred at −78° C. for 1 hr, the reaction mixture was warmed gradually to room temperature and stirred for 30 min. The mixture was again cooled to −78° C. and added dropwise a THF solution (25 mL) of Bu$_3$SnCl (32.5 g, 100 mmol) with stirring. The mixture was warmed gradually to room temperature and stirred for 10–12 hrs and then concentrated. Distillation (92° C., 0.5 torr) yielded 31.3 g (87.7 mmol) of 2-(tributylstannyl) furan (87% yield).

$^1$H NMR (CDCl$_3$, 200 MHz): δ 7.73 (d,J=2.8 Hz, 1H), 6.56 (dd, J=2.8, 5.8 Hz, 1H), 6.41 (d,J=5.8 H, 1H), 0.86–1.62 (m, 27H).

(2) Synthesis of dihydroxy-[2-(5-formylthienyl)]borane

Following the procedure for preparing dihydroxy-(2-furyl)borane as described in step (2) of Example 1, 18.6 g (100 mmol) of 2-(diethoxymethyl)thiophene (see step (1) of Example 1) was converted to dihydroxy-[2-(5-formylthienyl)] borane which was then used for the next reaction.

(3) Synthesis of 5-bromo-5'-formyl-2,2'-bithiophene

Following the procedure for preparing 5-bromo-2,2'-bifuran as described in step (4) of Example 1, 15.5 g (64 mmol) of 2,5-dibromothiophene was reacted with 2 g (14 mmol) of dihydroxy-[2-(5-formylthienyl)]borane obtained from the preceding reaction to yield 30% of 5-bromo-5'-formyl-2,2'-bithiophene.

$^1$H NMR (CDCl$_3$, 200 MHz): δ 7.01 (d,J=3.8 Hz, 1H), 7.09 (d,J=3.8 Hz, 1H), 7.16 (d,J=4.0 Hz, 1H), 7.63 (d,J=4.0 Hz, 1H), 9.85 (s,1H). The crude product was used for the next reaction without further purification.

(4) Synthesis of 5-formyl-5'-(2-furyl)-2,2'-bithiophene

Following the procedure for preparing 5-[2-(5-formyl) thienyl]-2,2'-bifuran as described in step (5) of Example 1, 0.27 g (1 mmol) of 5-bromo-5'-formyl-2,2'-bithiophene obtained from the preceding reaction was reacted with 0.85 g (2 mmol) of 2-(tributylstannyl)furan (see step (1) of Example 3) to yield 50% of the desired 5-formyl-5'-(2-fural)-2,2'-bithiophene (mp 81–82° C.).

$^1$H NMR (CDCl$_3$, 300 MHz): δ 6.46 (d,J=1.5, 3.3 Hz, 1H), 6.56 (d,J=3.3 Hz, 1H), 7.17 (d,J=3.9 Hz, 1H), 7.21 (d,J=3.9 Hz, 1H), 7.27 (d,J=3.9 Hz, 1H), 7.42 (d,J=1.5 Hz, 1H), 7.65 (d,J=3.9 Hz, 1H), 9.84 (s, 1H).

EXAMPLE 4

Synthesis of 5-(2-furyl)-5'-hydroxymethyl-2,2'-bithiophene

Following the procedure for preparing 5-[2-(5-hydroxymethyl)thienyl]-2,2'-bifuran as described in step (5) of Example 1, 0.08 g of 5-formyl-5'-(2-furyl)-2,2'-bithiophene was reduced to 0.064 g (80% yield) of 5-(2-furyl)-5'-hydroxymethyl-2,2'-bithiophene (mp>90° C., decomposed).

$^1$H NMR (CDCl$_3$, 300 MHz): δ 4.79 (s,2H), 6.43 (dd, J=1.6, 3.4 Hz, 1H), 6.49 (d,J=3.4 Hz, 1H), 6.90 (d,J=3.6 Hz, 1H), 7.02 (d,J=3.6 Hz, 1H), 7.06 (d,J=3.9 Hz, 1H), 7.12 (d,J=3.9 Hz, 1H), 7.39 (d,J=1.6 Hz, 1H); MS (m/z) 261 (M-1, 27), 245 (19), 203 (3), 179 (11), 167 (21), 149 (63), 121 (13), 83 (12), 60 (57), 44 (100).

EXAMPLE 5

Synthesis of 5-formyl-5'-[2-(5-formyl)furyl]-2,2'-bithiophene (1) Synthesis of 2-(diethoxymethyl)-5-(tributylstannyl)furan Following the procedure for preparing 2-(diethoxymethyl)-5-(tributylstannyl)-thiophene as described in step (1) of Example 1, 17 g (10 mmol) of 2-(diethoxymethyl)furan was converted to 32.6 g (82% yield) of 2-(diethoxymethyl)-5-(tributylstannyl) furan (bp 110° C., 1 torr).

$^1$H NMR (CDCl$_3$, 200 MHz): δ 0.83–3.60 (m, 27H), 3.51–3.60 (m, 4H), 5.56 (s, 1H), 6.39 (d,J=1.6 Hz, 1H), 6.47 (d,J=1.6 Hz, 1H).

(2) Synthesis of 5-formyl-5'-[2-(5-formyl)furyl]-2,2'-bithiophene

Following the procedure for preparing 5-[2-(5-formyl) thienyl]-2,2'-bifuran as described in step (5) of Example 1, 0.2 g (0.73 mmol) of 5-bromo-5-formyl-2,2'-bithiophene (see stp (3) of Example 3) was reacted with 0.336 g (0.73 mmol) of 2-(diethoxymethyl)-5-(tributylstannyl)furan obtained from the preceding reaction to yield 0.17 g (80% yield) of the desired product as brown solid (mp>165° C., decomposed).

$^1$H NMR (CDCl$_3$, 300 MHz): δ 6.72 (d, J=3.8 Hz, 1H), 7.29 (d,J=4.1 Hz, 2H), 7.33 (d,J=3.8 Hz, 1H), 7.45 (d,J=4.1 Hz, 1H), 7.68 (d,J=3.8 Hz, 1H), 9.63 (s,1H), 9.87 (s,1H); MS (m/z) 287 (M-1, 6), 254 (6), 222 (5), 190 (5), 149 (7), 133 (5), 86 (10), 69 (17), 41 (100).

EXAMPLE 6

Synthesis of 2-[2-(5-formyl)furyl]-5-(2-furyl)-thiophene (1) Synthesis of 2-(5-bromo)thienyl-5-formyl-furan To a 2-neck flask was placed 9.68 g (40 mmol) of 2,5-dibromothiophene (step (3) of Example 1), 0.86 g (10 mmol) of lithium bromide and 0.35 g (0.5 mmol) of catalyst PdCl$_2$ (PPh$_3$)$_2$, then added 100 mL of THF and 4.59 g (10 mmol) of 2-(diethoxymethyl)-5-(tributylstannyl)furan (step (1) of Example 5). The reaction mixture was cooled with liquid nitrogen and flashed with N$_2$. The system was then evacuated and replaced with N$_2$ several times. After 5 minutes, removed liquid nitrogen and the system was evacuated again and finally filled up with N$_2$. The reaction mixture was then heated at reflux for 15 hrs. TLC showed several fluorescent spots, among which, the less polar spot was identified as the desired monobromodimer and the more polar spot was self-coupled difurandialdehyde. Aqueous HCl (10%) was added to hydrolyze diethylacetal. After stirring for 10–20 minutes, TLC showed that 2 fluorescent spots remained. The mixture was extracted with Ether. The combined ether extracts were dried with anhydrous $MgSO_4$ and concentrated. Chromatograph yielded 1.5 g (58% yield) of the desired product as orange color solid (mp 80–82° C.).

$^1$H NMR ($CDCl_3$, 200 MHz): δ 6.60 (d,J=3.6 Hz, 1H), 7.04 (d,J=4.0 Hz, 1H), 7.23 (d,J=4.0 Hz, 1H), 7.25 (d,J=3.6 Hz, 1H), 9.59 (s, 1H).

(2) Synthesis of 2-[2-(5-formyl)furyl]-5-(2-furyl)-thiophene 0.2 g (0.77 mmol)of 2-(5-bromo)thienyl-5-formyl-furan obtained from the preceding reaction was coupled with 0.356 g (1 mmol) of 2-(tributylstannyl)furan (see step (1) Example 3) to yield 107 mg (57% yield) of the desired product as yellow color solid (mp 64–65° C.).

$^1$H NMR ($CDCl_3$, 200 MHz): δ 6.46 (dd, J=3.5, 2.0 Hz, 1H), 6.57(d,J=3.5 Hz, 1H), 6.64 (d,J=3.5 Hz, 1H), 7.20 (d,J=4.0 Hz, 1H), 7.27 (d,J=4.0 Hz, 1H), 7.71–7.44 (m, 2H), 9.59 (s, 1H); MS (m/z) 244 (M, 100), 216 (13), 187 (41), 159 (16), 115 (19), 89 (5), 69 (6).

EXAMPLE 7

Synthesis of 5-[2-(5-formyl)furyl]-2,2'-bithiophene 0.2 g (0.77 mmol) of 2-(5-bromo)thienyl-5-formyl-furan obtained from step (1) of Example 6 was coupled with 0.372 g (1 mmol) of 2-(tributylstannyl) thiophene to yield 156 mg (78% yield) of the desired product as orange color solid (mp 79–80° C.).

$^1$H NMR ($CDCl_3$, 200 MHz): δ 6.64 (dd, J=3.8 Hz, 1H), 7.03 (dd,J=3.4, 5.0 Hz, 1H), 7.14 (d,J=3.8 Hz, 1H), 7.20–7.27 (m, 3H), 7.40 (d,J=3.8 Hz, 1H), 9.59 (s, 1H); MS (m/z) 259 (M-1, 100), 232 (23), 203 (74), 171 (23), 127(7), 115 (10), 95 (6), 69 (23), 45 (23).

EXAMPLE 8

Synthesis of 5-formyl-2,2':5',2"-terfuran

Following the coupling procedure for preparing 2-(5-bromo)thienyl-5-formyl-furan as described in step (1) of Example 6, 1.38 g (3 mmol) of 2-(diethoxymethyl)-5-(tributylstannyl)furan (step (1) of Example 5) was coupled with 5-bromo-2,2'-bifuran (step (4) of Example 1) to yield 211 mg (31% yield) of the desired product as yellow color solid (mp 103–104° C.).

$^1$H NMR ($CDCl_3$, 200 MHz): δ 6.47 (dd,J=3.6, 1.6 Hz, 1H), 6.65 (d,J=3.6 Hz, 1H), 6.68 (d,J=3.8 Hz, 1H), 6.76 (d,J=3.8 Hz, 1H), 6.94 (d,J=3.8 Hz, 1H); 7.29 (d,J=3.8 Hz, 1H), 7.44 (d,J=1.6 Hz, 1H), 9.6 (s, 1H); MS (m/z) 228 (M, 100), 200 (10), 171 (43), 143 (10), 115(44), 95 (8), 89 (10), 63 (7), 51 (17).

EXAMPLE 9

Synthesis of 2,5-bis[2-(5-formyl)thienyl]furan

Following the procedure for preparing 5-[2-(5-formyl) thienyl]-2,2'-bifuran as described in Example 1, 0.23 g (1 mmol) of 2,5-dibromofuran (step (3) of Example 1) was coupled with 0.95 g (2 mmol) of 2-(diethoxymethyl)-5-(tributylstannyl)thiophene (step (1) of Example 1) to yield 0.17 g (60% yield) of the desired product as solid (mp 279–281° C.).

$^1$H NMR ($CDCl_3$, 200 MHz): δ 6.82 (s, 2H), 7.40 (d,J=4.0 Hz, 2H), 7.70 (d,J=4.0 Hz, 2H), 9.89 (s, 2H); MS (m/z) 287 (M-1, 10), 256 (6), 222 (9), 199 (5), 183 (7), 149 (22), 121 (18), 44 (100).

EXAMPLE 10

Synthesis of 2,5-bis[2-(5-hydroxymethyl)thienyl] furan

Following the procedure for preparing 5-[2-(5-hydroxymethyl)thienyl]-2,2'-bifuran as described in Example 2, 100 mg of 2,5-bis[2-(5-hydroxymethyl)thienyl] furan obtained from the preceding reaction was reduced to 87 mg (86% yield) of the desired product as solid (mp>140° C., decomposed).

$^1$H NMR ($CDCl_3$, 200 MHz): δ 4.81 (s, 4H), 6.50 (s, 2H), 6.92 (d,J=3.7 Hz, 2H), 7.14 (d,J=3.7 Hz, 2H); MS (m/z) 291 (M-1, 7), 256 (19), 228 (2), 213 (2), 167 (8), 149 (26) 129 (9), 43 (100).

EXAMPLE 11

Synthesis of 5,5"-diformyl-2,2':5',2"-terfuran

Following the procedure for preparing 5-[2-(5-formyl) thienyl]-2,2'-bifuran as described in step (5) of Example 1, 0.21 g (1 mmol) of 2,5-dibromofuran (step (3) of Example 1) was coupled with 0.91 g (2 mmol) of 2-(diethoxymethyl)-5-(tributylstannyl)furan (step (1) of Example 5) to yield 0.14 g (55% yield) of the desired product as solid (mp>172° C., decomposed).

$^1$H NMR ($CDCl_3$, 200 MHz): δ 6.85 (d, J=3.8 Hz, 2H) 7.00 (s, 2H); MS (m/z) 256 (M, 100), 228 (16), 199 (51), 190 (29), 162 (5), 133 (34), 115 (41).

EXAMPLE 12

Synthesis of 2,5-bis[2-(5-formyl)furyl]thiophene

Following the procedure for preparing 5-[2-(5-formyl) thienyl]-2,2'-bifuran as described in step (5) of Example 1, 0.24 g (1 mmol) of 2,5-dibromothiophene was coupled with 0.91 g (2 mmol) of 2-(diethoxymethyl)-5-(tributylstannyl) furan (step (1) of Example 5) to yield 0.13 g (50% yield) of the desired product as solid (mp 180–182° C.).

$^1$H NMR ($CDCl_3$, 200 MHz): δ 6.73 (d,J=3.9 Hz, 2H), 7.29 (d,J=3.9 Hz, 2H), 7.48 (s, 2H), 9.63 (s, 2H); MS (m/z) 271 (M-1, 11), 244 (1), 215 (6), 158 (2), 133 (14), 121 (6), 87 (12), 60 (53), 45 (100).

EXAMPLE 13

Synthesis of 2,5-bis[2-(5-hydroxymethyl)furyl]-thiophene

A THF solution (10 mL) of 2,5-bis[2-(5-formyl) furyl]-thiophene (41 mg), obtained from Example 12, was treated with excess amount of $NaBH_4$ and stirred at room temperature. The reaction was monitored by TLC till completion. After removal of THF under reduced pressure, water was added. The mixture was extracted with ethyl acetate. The combined ethyl acetate extracts were washed with brine, dried with $MgSO_4$, filtered and concentrated to yield 39 mg (93% yield) of the reduced product as yellow color solid.

$^1$H NMR ($CD_3OD$, 200 MHz): δ 4.53 (s, 4H), 6.36 (d,J=3.1 Hz, 2H), 6.52 (d,J=3.1 Hz, 2H), 7.18 (s, 2H); MS (m/z) 276 (M, 100), 259 (84), 217 (4), 207 (4), 171(4).

EXAMPLE 14

Synthesis of 5-hydroxymethyl-2,2':5',2"-terfuran

Similarly, 5-formyl-2,2':5',2"-terfuran, obtained from Example 8, was reduced to 5-hydroxymethyl-2,2':5',2"-terfuran, mp 75–77° C.

$^1$H NMR (CD$_3$COCD$_3$, 200 MHz): δ 4.56 (s, 2H), 6.39 (d,J=3.3 Hz, 1H), 6.55 (dd,J=1.8, 3.4 Hz, 1H), 6.62 (d,J=3.4 Hz, 1H), 6.66–6.71 (m, 3H), 7.59 (dd,J=0.5, 1.8 Hz, 1H). MS (m/z) 230 (M, 100), 213 (67), 171 (6), 115 (8), 71 (11), 43 (16), 31(13).

EXAMPLE 15

Synthesis of 5,5"-dihydroxymethyl-2,2':5',2"-terfuran

Similarly, 5,5"-diformyl-2,2':5',2"-terfuran, obtained from Example 11, was reduced to 5,5"-dihydroxymethyl-2, 2':5',2"-terfuran, mp 142–145° C.

$^1$H NMR (CD$_3$COCD$_3$, 200 MHz): δ 4.44 (t, J=5.0 Hz, 2H), 4.56 (d,J=5.0 Hz, 4H), 6.39 (d,J=3.3 Hz, 2H), 6.62 (d, J=3.3 Hz, 2H), 6.67 (s, 2H); MS (m/z) 230 (M, 100), 243 (79), 201 (3), 177 (3), 115 (4), 77(3).

EXAMPLE 16

Synthesis of 5-[2-(5-hydroxymethyl furyl]-2,2'-bithiophene

Similarly, 5-[2-(5-formyl)furyl]-2,2'-bithiophene, obtained from Example 3, was reduced to 5-[2-(5-hydroxymethylfuryl]-2,2'-bithiophene, mp 80–82° C.

$^1$H NMR (CDCl$_3$, 200 MHz): δ 4.63 (d,J=5.7 Hz, 2H) 6.34 (d,J=3.3 Hz, 1H), 6.43 (d,J=3.3 Hz, 1H), 7.00 (dd,J= 3.6, 5.1 Hz, 1H); 7.08 (d,J=3.8 Hz, 1H), 7.14 (d,J=3.8 Hz, 1H), 7.16 (dd,J=1.1, 3.6 Hz, 1H), 7.20 (d,d,J=1.1, 5.1 Hz, 1H); MS (m/z) 262 (100), 245 (79), 217 (5), 203 (15), 193 (5), 184(7), 171(7), 121(8).

EXAMPLE 17

Synthesis of 2-[2-(5-hydroxymethyl)furyl]-5-(2-furyl)-thiophene

Similarly, 2-[2-(5-formyl)furyl]-5-(2-furyl)-thiophene, obtained from Example 6, was reduced to 2-[2-(5-hydroxymethyl)furyl]-5-(2-furyl)-thiophene, mp 72–74° C.

$^1$H NMR (CDCl$_3$, 200 MHz): δ 4.63 (bs, 2H), 6.34 (d,J=3.5 Hz, 1H), 6.42(dd,J=1.7, 3.5 Hz, 1H), 6.34 (d,J=3.5 Hz, 1H); 6.49 (d,J=3.5 Hz, 1H), 7.15 (AA', 2H), 7.39 (d,J=1.7 Hz, 1H); MS(m/z) 246 (M, 100), 229 (80), 201 (5), 187 (14), 177 (7), 171 (7), 158(7), 121(8), 115(9), 77(4).

EXAMPLE 18

Screening of Compounds for Antitumor Activity

The cytotoxic activity of nine polyheterocyclic compounds, i.e., 5-[2-(5-formyl)thienyl]-2,2'-bifuran (obtained from Example 1), 5-[2-(5-hydroxymethyl) thienyl]-2,2'-bifuran (obtained from Example 2), 5-formyl-5'-(2-furyl)-2,2'-bithiophene (obtained from Example 3), 5-(2-furyl)-5'-hydroxymethyl-2,2'-bithiophene (obtained from Example 4), 5-formyl-5'-[2-(5-formyl)furyl]-2,2'-bithiophene (obtained from Example 5), 2-[2-(5-formyl) furyl]-5-(2-furyl)-thiophene (obtained from Example 6), 5-[2-(5-formyl)furyl]-2,2'-bithiophene (obtained from Example 7), 5,5"-diformyl-2,2':5',2"-terfuran (obtained from Example 11), and 2,5-bis[2-(5-formyl)furyl] thiophene (obtained from Example 12), were measured utilizing the cytotoxicity against a panel of sixty one different NCI human tumor cell lines.

The sixty one tumor cell lines used to test the antitumor activity of the above-listed polyheterocyclic compounds are listed below:

Leukemia
   CCRF-CEM, HL-60 (TB), K-562, MOLT-4, RPMI-8226, and SR.
Lung Cancer
   A549/ATCC, EKVX, HOP-62, HOP-92, NCI-H226, NCI-H23, NCI-H322M, NCI-H460, and NCI-H522.
Colon Cancer
   COLO 205, HCC-2998, HCT-116, HCT-15, HT-29, KM-12, and SW-620.
CNS Cancer
   SF-268, SF-295, SF-539, SNB-19, SNB-75, and U-251.
Melanoma
   LOX-IMVI, MALME-3M, M-14, SK-MEL-2, SK-MEL-28, SK-MEL-5, UACC-257, and UACC-62.
Ovarian Cancer
   IGR-OVI, OVCAR-3, OVCAR-4, OVCAR-5, OVCAR-8, and SK-OV-3.
Renal Cancer
   786-0, A-498, ACHN, CAKI-1, RXF-393, RXF-631, SN12C, TK-10, and U0-31.
Prostate Cancer
   PC-3 and DU-145.
Breast Cancer
   MCF 7, MCF7/ADR-RES, MDA-MB-231/ATCC, HS578T, MDA-MB-435, MDA-N, BT-549, and T-47D.

This NCI antitumor activity screening assay provides data regarding the general cytotoxicity of an individual compound. In particular, this type of assay is useful in identifying compounds which have enhanced cytotoxic activity against slow growing tumors as compared to faster growing tumor cells such as leukemia tumor cell lines. The identification of such compounds is critical since previously identified antitumor agents have low cytotoxic activity against slower growing tumors.

Antitumor cytotoxicity data for the National Cancer Institute human tumor cell panels can be expressed in a graphic pattern (mean graph) to display differential cell growth inhibition [K. D. Paull, R. H. Shoemaker, L. Hodes, A. Monks, D. A. Scudiero, L. Rubinstein, J. Plowman and M. R. Boyd, J. Natl. Cancer Inst., 81, 1088, 1989]. In the meangraph, the arithmetic mean of the logarithm of the GI$_{50}$ (50% growth inhibition), TGI (total growth inhibition), or LC$_{50}$ (50% lethal concentration) values is used as an anchor point. Relative cytotoxicity is displayed by projecting bars to the right or left of the mean, depending on whether cell sensitivity to a test compound is more or less than average. The length of a bar is indicative of differential cytotoxicity against a specific type of tumor cells or tumor panels.

The antitumor cytotoxicity of the polyheterocyclic compounds tested in the in vitro assays was measured by a microculture assay using either 3-(4,5-dimethylthiazol-2-yl)-2,5-diphenyltetrazolium bromide ("MTT") or sulforhodamine B ("SRB") [M. R. Boyd, in "Principle of Practice of Oncology," J. T. Devita, S. Hellman, S. A. Rosenberg (Eds.) Vol. 3, PPO Update, No. 10, 1989]. This assay has an advantage over in vivo assay in that results are obtained within a week as opposed to several months. The assay was carried out in 96-well microtiter plates. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbout, J. G. Mayo, R. H. Shoemaker and M. R. Boyd, Cancer Res., 48, 589, 1988]. Thus, only live cells are stained and can be measured at 570 nm. The SRB assay is based on the binding of the anionic group to the basic amino acid residues of cellular proteins after exposure of tumor cells to drug for 2 days [P. Skehan, R. Storeng, D. Scudiero, A. Monks, J. McMahon, D. Vistica, J. T. Warren, H. Bohesch, S. Kenney and M. R. Boyd, J. Nat. Cancer Inst., 82, 1107, 1990]. Thus, the total protein (viability) can be measured at 564 nm. Antitumor cytotoxicity is reported as $GI_{50}$, effect drug dose at which cell growth is retarded to 50% of control culture of tumor cells. The active compounds are defined as those compounds having $GI_{50}$ values that are less than $10^{-4}$ M.

All nine tested compounds were found to be active. Take 5-(2-furyl)-5'-hydroxymethyl-2,2'-bithiophene, for example. It exhibited GIo values lower than $10^{-4}$ M for all tested cell lines, with the values lower than $10^{-8}$ M for 12 cell lines. Among the nine tested compounds, 2,5-bis[2-(5-formyl)furyl]thiophene is the least potent. Yet, it still exhibited $GI_{50}$ values lower than $10^{-4}$ M for as many as 8 cell lines. In terms of potency, 5-formyl-5'-[2-(5-formyl)furyl]-2,2'-bithiophene is only better than 2,5-bis[2-(5-formyl)furyl]thiophene and exhibited antitumor activity against 30 cell lines. Of note, it was unexpected that 5,5"-diformyl-2,2':5', 2"-terfuran, despite its structural similarities with 2,5-bis[2-(5-formyl)furyl] thiophene, were found to be far more potent and effective in inhibiting the growth of all tested cell lines.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For examples, salts and esters of novel polyheterocyclic compounds disclosed herein are within the scope of this invention. Thus, other embodiments are also within the claims.

What is claimed is:

1. A polyheterocyclic compound of the following formula:

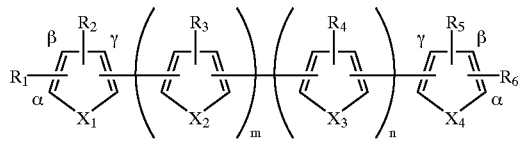

wherein
each of $X_1$, $X_2$, $X_3$, and $X_4$, independently, is O, S, NH, or $N(C_{1-6}$ alkyl);
each of $R_1$, $R_2$, $R_5$, and $R_6$, independently, is H, CN, $NO_2$, $C_{1-4}$ haloalkyl, $CR^aR^b(CH_2)_oNR^cR^d$, $NR^cR^d$, $CR^a=NR^c$, $CR^a=N^+R^cR^d$, $CR^aR^b(CH_2)_oOR^e$, $CR^aR^b(CH_2)_oO(C_{1-7}$ acyl), $CR^aR^b(CH_2)_oO$ (tetrahydropyranyl), $OR^e$, $O(C_{1-7}$ acyl), $C(O)R^e$, $C(O)OR^e$, $CH(OR^e)_2$, $CH=CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are $—(CH_2)_4—$, $—(CH_2)_5—$, or $—(CH_2)_2NH(CH_2)_2—$; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;
each of m and n, independently, is 0 or 1;
provided that at least one of $X_1$, $X_2$, $X_3$, and $X_4$ is O, NH, or $N(C_{1-6}$ alkyl), $X_1$, $X_2$, $X_3$, and $X_4$ are not all identical, and at least one of $R_1$, $R_2$, $R_5$, and $R_6$ is a substituent.

2. The compound of claim 1 wherein
each of $X_1$, $X_2$, $X_3$, and $X_4$, independently, is O or S;
each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are $—(CH_2)_4—$, $—(CH_2)_5—$, or $—(CH_2)_2NH(CH_2)_2—$; each $R^e$, independently, is H; $R^f$ is $C_{4-5}$ cyclic amine;
each of $R_3$ and $R_4$, independently, is $CH_2OH$ or $CH_2NH_2$;
m is 1; and
n is 0.

3. The compound of claim 2 wherein each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are $—(CH_2)_4—$, $—(CH_2)_5—$, or $—(CH_2)_2NH(CH_2)_2—$; and each $R^e$, independently, is H.

4. The compound of claim 1 wherein $R_1$ is H, $R_2$ is H, and each of $R_5$ and $R_6$, independently, is a substituent.

5. The compound of claim 4 wherein
each of $X_1$, $X_2$, $X_3$, and $X_4$, independently, is O or S;
each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are $—(CH_2)_4—$, $—(CH_2)_5—$, or $—(CH_2)_2NH(CH_2)_2—$; each $R^e$, independently, is H; $R^f$ is $C_{4-5}$ cyclic amine;
each of $R_3$ and $R_4$, independently, is $CH_2OH$ or $CH_2NH_2$;
m is 1; and
n is 0.

6. The compound of claim 5 wherein each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are $—(CH_2)_4—$, $—(CH_2)_5—$, or $—(CH_2)_2NH(CH_2)_2—$; and each $R^e$, independently, is H.

7. The compound of claim 1 wherein $R_1$ is H, $R_5$ is H, and each of $R_2$ and $R_6$, independently, is a substituent; provided that if $R_2$ is a α-substituent, $R_6$ must be a β- or γ-substituent; if $R_2$ is a β-substituent, $R_6$ must be a α- or γ-substituent; and if $R_2$ is a γ-substituent, $R_6$ must be a α- or β-substituent.

8. The compound of claim 7 wherein
each of $X_1$, $X_2$, $X_3$, and $X_4$, independently, is O or S;
each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are $—(CH_2)_4—$, $—(CH_2)_5—$, $—(CH_2)_2NH(CH_2)_2—$; each $R^e$, independently, is H; $R^f$ is $C_{4-5}$ cyclic amine;
each of $R_3$ and $R_4$, independently, is $CH_2OH$ or $CH_2NH_2$;
m is 1; and
n is 0.

9. The compound of claim 8 wherein each of $R_1$, $R_2$, $R_5$, and $R_6$, independently, is $CR^aR^b(CH_2)_oNR^cR^d$ or $CR^aR^b$ $(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

10. The compound of claim 1 wherein at least two of 2 the heterocyclic moieties are joined to each other via an α-β linkage.

11. The compound of claim 10 wherein
each of $X_1$, $X_2$, $X_3$, and $X_4$, independently, is O or S;
each of $R_1$, $R_2$, $R_3$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}$ acyl) $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, —$(CH_2)_2NH(CH_2)_2$—; each $R^e$, independently, is H; $R^f$ is $C_{4-5}$ cyclic amine;
each of $R_3$ and $R_4$, independently, is $CH_2OH$ or $CH_2NH_2$;
m is 1; and
n is 0.

12. The compound of claim 11 wherein each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

13. A polyheterocyclic compound of the following formula:

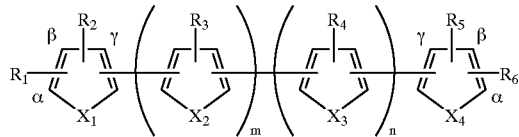

wherein
each of $X_1$, $X_2$, $X_3$, and $X_4$, independently, is O, S, NH, or $N(C_{1-6}$ alkyl);
each of $R_1$, $R_2$, $R_5$, and $R_6$, independently, is H, halogen, CN, $NO_2$, $C_{1-4}$ haloalkyl, $CR^aR^b(CH_2)_oNR^cR^d$, $NR^cR^d$, $CR^a=NR^c$, $CR^a=N^+R^cR^d$, $CR^aR^b(CH_2)_oOR^e$, $CR^aR^b(CH_2)_oO(C_{1-7}acyl)$, $CR_aR_b(CH_2)_oO$ (tetrahydropyranyl), $OR^e$, $O(C_{1-7}$ acyl), $C(O)R^e$, $C(O)OR^e$, $CH(OR^e)_2$, $CH=CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are —$(CH_2)_4$—, —$(CH_2)_5$—, or —$(CH2)_2NH(CH2)_2$—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;
each of $R_3$ and $R_4$, independently, is H, $C_{1-6}$ alkyl, CHO, $CH_2OH$, or $CH_2NH_2$;
m is 1; and
n is 0 or 1;
provided that at least one of $X_1$, $X_2$, $X_3$, and $X_4$ is O, NH, or $N(C_{1-6}$ alkyl) and at least one of $R_1$, $R_2$, $R_5$, and $R_6$ is a β-substituent.

14. The compound of claim 13 wherein
each of $X_1$, $X_2$, $X_3$, and $X_4$, independently, is O or S;
each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or —$(CH_2)_4$—, —$(CH_2)_5$—, or —$(CH_2)_2NH(CH_2)_2$—; each $R^e$, independently, is H; $R^f$ is $C_{4-5}$ cyclic amine;
each of $R_3$ and $R_4$, independently, is $CH_2OH$ or $CH_2NH_2$; and
n is 0.

15. The compound of claim 14 wherein
each of $X_1$, $X_2$, $X_3$, and $X_4$, independently, is O; and
each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

16. The compound of claim 13 wherein at least two of the heterocyclic moieties are joined to each other via an α-β linkage.

17. The compound of claim 16 wherein
each of $X_1$, $X_2$, $X_3$, and $X_4$, independently, is O or S;
each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together are —$(CH_2)_4$—, —$(CH_2)_5$—, or —$(CH_2)_2NH(CH_2)_2$—; each $R^e$, independently, is H; $R^f$ is $C_{4-5}$ cyclic amine;
each of $R_3$ and $R_4$, independently, is $CH_2OH$ or $CH_2NH_2$; and
n is 0.

18. The compound of claim 17 wherein
each of $X_1$, $X_2$, $X_3$, and $X_4$, independently, is O or S;
each of $R_1$, $R_2$, $R_5$, and $R_6$, independently, is $CR^aR^b(CH_2)_oNR^cR^d$ or $CR^aR^b(CH_2)_oOR^e$, $R^c$ and $R^d$, together, are —$(CH_2)_4$—, —$(CH_2)_5$—, or —$(CH_2)_2NH(CH_2)_2$—; and each $R^e$, independently, is H.

19. A method of treating tumor to a patient in need thereof, said method comprising administering a pharmaceutical composition comprising an effective amount of a polyheterocyclic compound of the following formula:

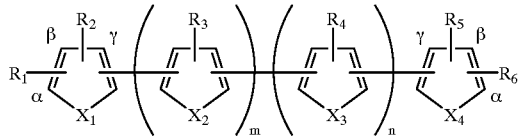

wherein
each of $X_1$, $X_2$, $X_3$, and $X_4$, independently, is O, S, NH, or $N(C_{1-6}$ alkyl);
each of $R_1$, $R_2$, $R_5$, and $R_6$, independently, is H, $C_{1-6}$ alkyl, halogen, CN, $NO_2$, $C_{1-4}$ haloalkyl, $CR^aR^b(CH_2)_oNR^cR^d$, $NR^cR^d$, $CR^a=NR^c$, $CR^a=N^+R^cR^d$, $CR^aR^b(CH_2)_oOR^e$, $CR^aR^b(CH_2)_oO(C_{1-7}$ acyl), $CR^aR^b(CH_2)_oO$(tetrahydropyranyl), $OR^e$, $O(C_{1-7}$ acyl), $C(O)R^e$, $C(O)OR^e$, $CH(OR^e)_2$, $CH=CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are —$(CH_2)_4$—, —$(CH_2)_5$—, or —$(CH_2)_2NH(CH_2)_2$—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;
each of $R_3$ and $R_4$, independently, is H, $C_{1-6}$ alkyl, CHO, $CH_2OH$, or $CH_2NH_2$;

each of m and n, independently, is 0 or 1;

provided that at least one of $X_1$, $X_2$, $X_3$, and $X_4$ is O, NH, or N($C_{1-6}$ alkyl), and at least one of $R_1$, $R_2$, $R_5$, and $R_6$ is a substituent;

and a pharmaceutically acceptable carrier thereof.

20. A pharmaceutical composition comprising an effective amount of a polyheterocyclic compound of the following formula:

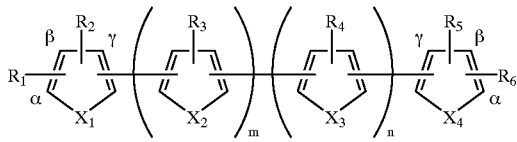

wherein each of $X_1$, $X_2$, $X_3$, and $X_4$, independently, is O or S;

each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, —$(CH_2)_2NH(CH_2)_2$—; each $R^e$, independently, is H; $R^f$ is $C_{4-5}$ cyclic amine;

each of $R_3$ and $R_4$, independently, is $CH_2OH$ or $CH_2NH_2$; and m is 0 or 1 and n is 0;

provided that at least one of $X_1$, $X_2$, $X_3$, and $X_4$ is O;

and a pharmaceutically acceptable carrier thereof.

21. The composition of claim 20 wherein each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

22. A pharmaceutical composition comprising an effective amount of a polyheterocyclic compound of the following formula

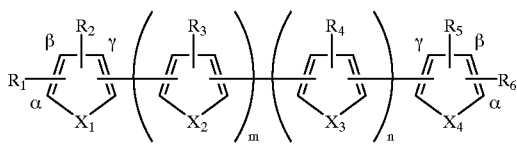

wherein each of $X_1$, $X_2$, $X_3$, and $X_4$, independently, is O, S, NH, or N($C_{1-6}$ alkyl);

R1 is H, $R_2$ is H, and each of $R_5$ and $R_6$, independently, is $C_{1-6}$ alkyl, halogen, CN, $NO_2$, $C_{1-4}$ haloalkyl, $CR^aR^b(CH_2)_oNR^cR^d$, $NR^cR^d$, $CR^a$=$NR^c$, $CR^a$=$N^+R^cR^d$, $CR^aR^b(CH_2)_oOR^e$, $CR^aR^b(CH_2)_oO(C_{1-7}$ acyl), $CR^aR^b(CH_2)_oO$(tetrahydropyranyl), $OR^e$, $O(C_{1-7}$ acyl), $C(O)R^e$, $C(O)OR^e$, $CH(OR^e)_2$, CH=$CHCOOR^e$, or $CH_2R^f$; each of $R^a$ and $R^b$, independently, is H or $C_{1-6}$ alkyl; each of $R^c$ and $Rd^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are —$(CH_2)_4$—, —$(CH_2)_5$—, or —$(CH_2)_2NH(CH_2)_2$—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;

each of m and n, independently, is 0 or 1;

provided that at least one of $X_1$, $X_2$, $X_3$, and $X_4$ is O, NH, or N($C_{1-6}$ alkyl);

and a pharmaceutically acceptable carrier thereof.

23. The composition of claim 22 wherein each of $X_1$, $X_2$, $X_3$, and $X_4$, independently, is O or S;

each of $R_1$, $R_2$, $R_5$, and $R_6$, independently, is $CR^aR^b(CH_2)_oNR^cR^d$, $CR^a$=$NR^c$, $CR^aR^b(CH_2)_oOR^e$, $CR^aR^b(CH_2)_oO(C_{1-7}$ acyl), $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine;

each of $R_3$ and $R_4$, independently, is $CH_2OH$ or $CH_2NH_2$; and n is 0.

24. The composition of claim 23 wherein each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

25. A pharmaceutical composition comprising an effective amount of a polyheterocyclic compound of the following formula:

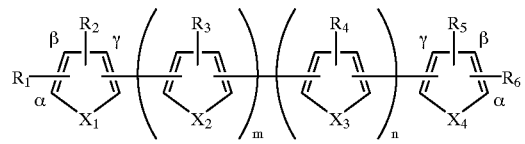

wherein each of $X_1$, $X_2$, $X_3$, and $X_4$, independently, is O, S, NH, or N($C_{1-6}$ alkyl);

$R_1$ is H, $R_5$ is H, and each of $R_2$ and $R_6$, independently, is $C_{1-6}$ alkyl, halogen, CN, $NO_2$, $C_{1-4}$ haloalkyl, $CR^aR^b(CH_2)_oNR^cR^d$, $NR^cR^d$, $CR^a$=$NR^c$, $CR^a$=$N^+R^cR^d$, $CR^aR^b(CH_2)_oOR^e$, $CR^aR^b(CH_2)_oO(C_{1-7}$ acyl), $CR^aR^b(CH_2)_oO$(tetrahydropyranyl), $OR^e$, $O(C_{1-7}$ acyl), $C(O)R^e$, $C(O)OR^e$, $CH(OR^e)_2$, CH=$CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R_c$ and $R_d$, together, are —$(CH_2)_4$—, —$(CH_2)_5$—, or —$(CH_2)_2NH(CH_2)_2$—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;

each of m and n, independently, is 0 or 1;

provided that at least one of $X_1$, $X_2$, $X_3$, and $X_4$ is O, NH, or N($C_{1-6}$ alkyl) and that if $R_2$ is a α-substituent, $R_6$ must be a β- or γ-substituent; if $R_2$ is a β-substituent, $R_6$ must be a α- or γ-substituent; and if $R_2$ is a γ-substituent, $R_6$ must be a α- or β-substituent;

and a pharmaceutically acceptable carrier thereof.

26. The composition of claim 25 wherein each of $X_1$, $X_2$, $X_3$, and $X_4$, independently, is O or S;

each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}\ acyl)$, $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine;

each of $R_3$ and $R_4$, independently, is $CH_2OH$ or $CH_2NH_2$; and n is 0.

27. The composition of claim 26 wherein each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

28. A pharmaceutical composition comprising an effective amount of a polyheterocyclic compound of the following formula:

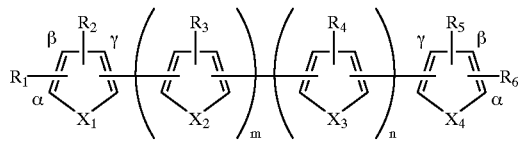

wherein each of $X_1$, $X_2$, $X_3$, and $X_4$, independently, is O, S, NH, or $N(C_{1-6}\ alkyl)$;

each of $R_1$, $R_2$, $R_5$, and $R_6$, independently, is H, $C_{1-6}$ alkyl, halogen, CN, $NO_2$, $C_{1-4}$ haloalkyl, $CR^aR^b(CH_2)_oNR^cR^d$, $NR^cR^d$, $CR^a=NR^c$, $CR^a=N^+R^cR^d$, $CR^aR^b(CH_2)_oOR^e$, $CR^aR^b(CH_2)_oO(C_{1-7}\ acyl)$, $CR^aR^b(CH_2)_oO(tetrahydropyranyl)$, $OR^e$, $O(C_{1-7}\ acyl)$, $C(O)R^e$, $C(O)OR^e$, $CH(OR^e)_2$, $CH=CHCOOR^e$, or $CH_2R^f$; each of $R^a$ and $R^b$, independently, is H or $C_{1-6}$ alkyl; each of $R^c$ and $R^d$, independently, is H, $C_{1-6}$ alkyl, $(CH_2)_pN(R^e)_2$, $(CH_2)_pOH$, $(CH_2)_pNH(CH_2)_qOH$, or $C_{4-5}$ cyclic amine, or $R^c$ and $R^d$, together, are —$(CH_2)_4$—, —$(CH_2)_5$—, or —$(CH_2)_2NH(CH_2)_2$—; each $R^e$, independently, is H or $C_{1-6}$ alkyl; $R^f$ is $C(O)R^e$, CN, $NO_2$, $C_{4-5}$ cyclic amine, or $C(O)OR^e$; and each of o, p, and q, independently, is 0, 1, 2, or 3;

each of $R_3$ and $R_4$, independently, is H, $C_{1-6}$ alkyl, CHO, $CH_2OH$, or $CH_2NH_2$;

each of m and n, independently, is 0 or 1;

provided that at least one of $X_1$, $X_2$, $X_3$, and $X_4$ is O, NH, or $N(C_{1-6}\ alkyl)$, and at least one of $R_1$, $R_2$, $R_5$, and $R_6$ is a substituent, and at least two of the heterocyclic moieties are joined to each other via an α-β linkage;

and a pharmaceutically acceptable carrier thereof.

29. The composition of claim 28 wherein each of $X_1$, $X_2$, $X_3$, and $X_4$, independently, is O or S;

each of $R_1$, $R_2$, $R_5$, and $R_6$, independently, is $CR^aR^b(CH_2)_oNR^cR^d$, $CR^a=NR^c$, $CR^aR^b(CH_2)_oOR^e$, $CR^aR^b(CH_2)_oO(C_{1-7}\ acyl)$, $C(O)R^e$, or $C(O)OR^e$; each of $R^a$ and $R^b$, independently, is H; each of $R^c$ and $R^d$, independently, is H, $(CH_2)_pN(R^e)_2$, $(CH_2)_pOH$, $(CH_2)_pNH(CH_2)_qOH$, or $R^c$ and $R^d$, together, are —$(CH_2)_4$—, —$(CH_2)_5$—, or —$(CH_2)_2NH(CH_2)_2$—; each $R^e$, independently, is H; $R^f$ is $C_{4-5}$ cyclic amine;

each of $R_3$ and $R_4$, independently, is $CH_2OH$ or $CH_2NH_2$; and n is 0.

30. The composition of claim 29 wherein each of $X_1$, $X_2$, $X_3$, and $X_4$, independently, is O; and each of $R_1$, $R_2$, $R_5$, and $R_6$, independently, is $CR^aR^b(CH_2)_oNR^cR^d$ or $CR^aR^b(CH_2)_oOR^e$; $R^c$ and $R^d$, together, are —$(CH_2)_4$—, —$(CH_2)_5$—, or —$(CH_2)_2NH(CH_2)_2$—; and each $R^e$, independently, is H.

31. The compound of claim 1 wherein each of $X_1$, $X_2$, $X_3$, and $X_4$, independently, is O or S; provided that at least one of $X_1$, $X_2$, $X_3$, and $X_4$ is O, $X_1$, $X_2$, $X_3$, and $X_4$ are not all identical, and at least one of $R_1$, $R_2$, $R_5$, and $R_6$ is a substituent.

32. The compound of claim 13 wherein each of $X_1$, $X_2$, $X_3$, and $X_4$, independently, is O or S; provided that at least one of $X_1$, $X_2$, $X_3$, and $X_4$ is O, and at least one of $R_1$, $R_2$, $R_5$, and $R_6$ is a β-substituent.

33. The method of claim 19 wherein each of $X_1$, $X_2$, $X_3$, and $X_4$, independently, is O or S; provided that at least one of $X_1$, $X_2$, $X_3$, and $X_4$ is O, and at least one of $R_1$, $R_2$, $R_5$, and $R_6$ is a substituent.

* * * * *